United States Patent [19]

Amirav

[11] Patent Number: 5,153,673
[45] Date of Patent: Oct. 6, 1992

[54] PULSED FLAME ANALYZING METHOD AND DETECTOR APPARATUS FOR USE THEREIN

[76] Inventor: Aviv Amirav, 58 Bialik Avenue, 47205 Ramat Hasharon, Israel

[21] Appl. No.: 749,732

[22] Filed: Aug. 26, 1991

[30] Foreign Application Priority Data

Sep. 9, 1990 [IL] Israel .................................... 95617

[51] Int. Cl.$^5$ ............................................. G01N 21/72
[52] U.S. Cl. ................................... 356/315; 356/417
[58] Field of Search ................................ 356/315, 417

[56] References Cited

U.S. PATENT DOCUMENTS 3,625,614 12/1969 Herrmann et al. ................ 356/315
3,740,154 6/1973 Green ................................. 356/315

OTHER PUBLICATIONS

Herrmann, *Fresenius' Zeitschrift fur Analytische Chemie*, Band 212, Heft 1, 1965, pp. 1–15.
Rüdiger et al., *Analyst*, vol. 94, 1969, pp. 204–208.
Bojovic et al., *Spectrochimica Acta*, vol. 27 B, No. 9, Sep. 1972, pp. 385–390.
Kittelson et al., *Atmospheric Environment*, vol. 12, 1978, pp. 105–111.
Steele et al., *Applied Spectroscopy*, vol. 40, No. 3, Mar.-/Apr. 1986, pp. 357–363.
Mossotli et al., *Applied Spectroscopy*, vol. 25, No. 3, May/Jun. 1971, pp. 331–341.
Neu et al., *Messtechnik*, Jul. 1968, pp. 154–159.

Primary Examiner—F. L. Evans
Attorney, Agent, or Firm—Benjamin J. Barish

[57] ABSTRACT

A pulsed flame method and apparatus for analyzing a sample, by introducing the sample into a combustible gas mixture, igniting the combustible gas mixture to produce a pulsed flame and detecting a characteristic of the resulting pulsed flame to determine the identity and/or concentration of one or more chemical substances in the sample.

34 Claims, 8 Drawing Sheets

PULSED FLAME ANALYZING METHOD AND DETECTOR APPARATUS FOR USE THEREIN

FIELD AND BACKGROUND OF THE INVENTION

The present invention relates to flame analyzing methods and apparatus, and particularly to a method and detector apparatus for detecting the presence and-/or concentration of one or more chemical substances therein by igniting a combustible gas mixture containing the sample to produce a flame, and detecting a characteristic of the resulting flame.

Flame based detectors for gas chromatographs (GC) and air impurities are extensively utilized in chemical analysis, and constitute the major selective molecular detectors in use today. Most notable are: (a) the flame ionization detector (FID), which is the most commonly used GC detector, and which is selective for organic molecules; (b) the flame phototometer detector (FPD), which is used for the selective detection of sulfur and phosphorus containing molecules; and (c) the atomic absorption detector (AAD), which is used for trace metal analysis.

The conventional detectors of this type utilize a continuous flame produced by the continuous combustion of gasses, usually hydrogen and oxygen (alone or in air). The detected molecule, if introduced into the flame, may indicate its presence by the formation of charge carriers (positive ions, negative ions, or electrons), or by electromagnetic radiation emission, e.g., ultraviolet (UV), visible or infrared (IR). Alternatively, the combustion can create new species which are amenable to easier detection in spectroscopic techniques, such as fluorescence excitation or atomic and molecular absorption spectroscopy in the UV, visible, or IR spectral ranges. These and other flame effects are referred to as characteristics of the flame.

OBJECTS AND BRIEF SUMMARY OF THE INVENTION

An object of the present invention is to provide an improved flame chemical analyzing method having a number of significant advantages over the presently used methods, as will be described more particularly below.

According to the present invention, there is provided a flame method of analyzing a sample by introducing the sample into a combustible gas mixture, igniting the combustible gas mixture to produce a flame, and detecting a characteristic of the resulting flame to determine the identity and/or concentration of one or more chemical substances in the sample, characterized in that the flame is a pulsed flame.

As will be described below, the sample may be or include impurities in gasses or air, the output of a GC, aerosol of organic liquids outputted from a liquid chromatograph (LC), water aerosol with metal ions, etc.

As will also be described more particularly below, the foregoing pulsed flame method has a number of advantages over the conventional continuous flame methods, including the following:

(1) Increased sensitivity, because of much higher peak current or light emission (or species generation), and the reduction of long-term DC noise and drift (amplifier noise). In many applications, the integrated signal may be the same as in a continuous flame, but the noise is reduced considerably because of the reduced time of its integration, and therefore the signal-to-noise ratio is considerably improved.

(2) Increased selectivity, because of the possiblity of separating in time the desired signal from unwanted background flame noise.

(3) Addition of molecular and functional group information, because of the time dependence of the pulsed signal.

(4) Substantial decrease in fuel consumption, since there is no need, as in a continuous flame, to hold or keep the flame.

(5) Virtual elimination of flame-out problems, due to repetitive or continuous ignition.

The foregoing advantages are important in many applications of flame chemical analysis, but the reduced fuel comsumption is particularly important in portable gas detectors. Thus, fuel saving can be achieved by arbitrarily reducing the hydrogen flow, or by operating a pulsed hydrogen valve at a low repetition rate. In certain applications, the hydrogen can be replaced by a liquified gas, such as propane, wherein time separation can be achieved by the desired flame characteristic from the fuel gas effect. One example is the pulsed flame photometric detection of phosphorus compounds in a propane/air pulsed flame, achieved in our laboratory.

Various techniques are described below for producing the pulsed flame. According to one described technique, the sample and combustible gas mixture are continuously introduced into a flame chamber having a continuously energized igniter and having a volume which allows flame propagation in the chamber at a rate which, compared to the rate of introduction of the combustible gas mixture, causes the flame to self-terminate and then to re-ignite, to thereby produce the pulsed flame; i.e., the flame velocity is higher than the combustible gas velocity, so that the flame propagates and consumes all the combustible gasses which results in self-termination of the flame. The key element in the flame self-termination is the flame behaviour near the gas sources. An efficient self-termination can be achieved by a separate introduction of the fuel and oxidant gasses into the mixing volume of the pulsed flame chamber. Alternatively, the combustible gas mixture may be supplied through a small nozzle that prevents flame propagation through it by its small diameter, or by a wire or mesh perturbation near it. A metal frit or sintered glass can also serve as a flame arrestor. It is to be noted that a flame cannot propagate through a narrow (i.e., less than 1 mm inner diameter) unheated hole or tube.

According to a second described technique, the combustible gas mixture is fed under the control of pulsed-operated valve means, to thereby produce the pulsed flame. In a third described technique, the combustible gas mixture is ignited by pulsed-energized igniter means, to thereby produce the pulsed flame in a self-terminating flame chamber.

Also described below are various characteristics of the resulting flame which are detected in order to determine the identity and/or concentration of the chemical substance. According to the described techniques, the detected characteristic may be: charge carriers formed by the pulsed flame; electromagnetic radiation, particularly temporal light (UV, visible or IR) emitted from the pulsed flame; thermionic ions emitted from a surface by the pulsed flame; lamp-induced fluorescence induced by the pulsed flame; light absorption by species resulting from the pulsed flame; the effect on ion formation in an ion mobility spectrometer and its preparation and triggering affect on plasma emission induced by the pulsed flame.

According to still further described features, the flame may be selectively controlled to operate according to either a pulsed flame mode, or a continuous flame mode, e.g., in applications where a continuous flame is considered to be more stable.

In most applications of the pulsed flame technique, the pulses would be periodic with each flame duration at least one order, and preferably several orders, of magnitude less than the intervals between flames. The pulses, however, could also be aperiodic. Preferably, the durations of the flame pulses are from 40 microseconds to 40 milliseconds, and their frequency is up to 200 Hz. The trigger for the flame characteristic signal processing can be obtained by an auxiliary UV photodiode, by an ion collector signal initiated by organic impurities, or simply by self-triggering from the characteristic signal due to the effect of the pure flame. In case of pulsed ignition, the trigger control serves for the triggering of the signal processor as well. In many applications, the trapping and desorption of sample molecules would be performed between the flame pulses.

According to another aspect of the invention, there is provided a flame based detector for use in analyzing a sample in order to determine the identity and/or concentration of one or more chemical substances therein, comprising: feeding means for introducing the sample into a combustible gas mixture, igniter means for igniting the combustible gas mixture to produce a flame, and detector means for detecting a characteristic of the resulting flame to determine the identity and/or concentration of one or more chemical substances in the sample; characterized in that said apparatus includes control means for causing said flame to be a pulsed flame.

Further features and advantages of the invention will be apparent from the description below.

BRIEF DESCRIPTION OF THE DRAWINGS

The invention is herein described, by way of example only, with reference to the accompanying drawings, wherein.

DESCRIPTION OF PREFERRED EMBODIMENTS

Figure 1:
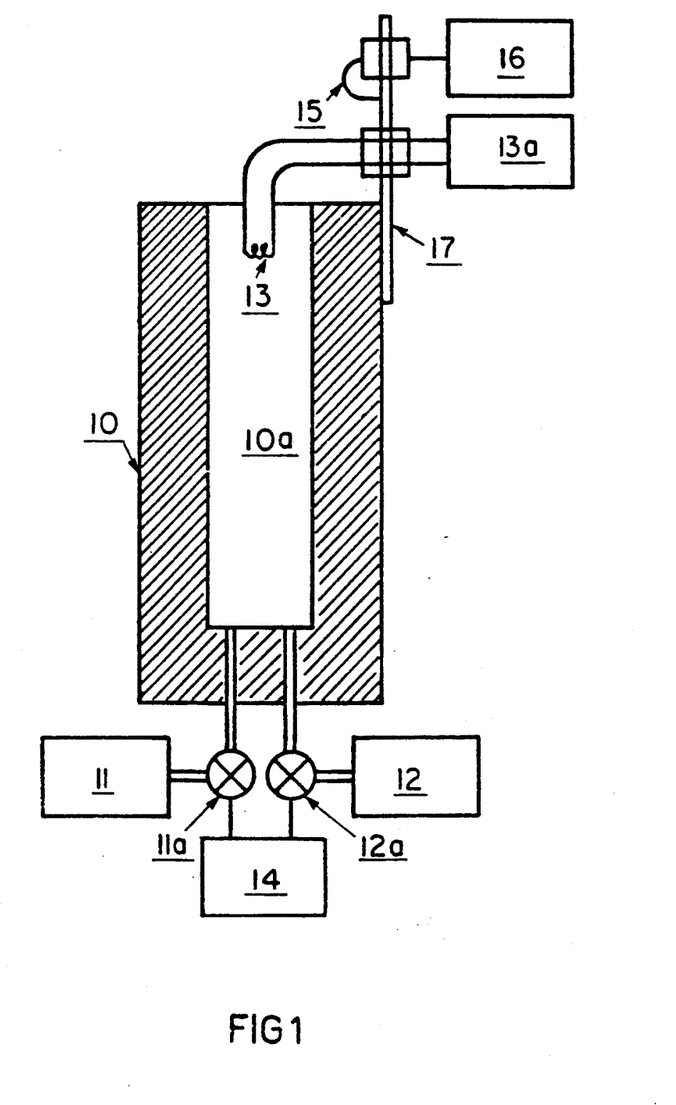
FIG. 1 is a schematic diagram of a pulsed flame ionization detector (PFID) constructed in accordance with the invention.

The pulsed flame ionization detector (PFID) illustrated in FIG. 1, and therein generally designated 10, comprises a flame chamber 10a fed by a fuel (e.g., hydrogen) from a fuel supply 11 under the control of a valve 11a, and with oxygen or air from a supply 12 under the control of a valve 12a. The sample containing the chemical substance to be detected is preferably mixed with the fuel in the fuel supply 11; however, it could be mixed with the oxygen (or air) in the supply 12, or it could be separately fed into the flame chamber 10a.

A flame igniter 13 is provided at the other end of the flame chamber 10a. Igniter 13 may be a continuously-heated wire energized from a power supply 13a. The ignited gas mixture, including the chemical substance to be detected, forms a flame which is propagated from the igniter 13 to the opposite end of the chamber, and is self-terminated so as to produce a pulsed flame.

Preferably, the self-termination of the flame is produced by continuously feeding the combustible gas mixture from sources 11 and 12, and continuously energizing the igniter 13, but designing the volume of the flame chamber 10a so as to allow a faster flame propagation therein than the rate of feeding and flow of the combustible gas mixture. However, the pulsed flame may also be produced by pulsing one of the valves 11a, 12a (usually the gas that does not contain the sample), via valve control unit 14, to feed the combustible gas mixture in the form of pulses into the flame chamber 10a. A further alternative would be to control the power supply 13a of the igniter 13, to energize the igniter by pulses, rather than continuously.

The charge carriers (e.g., ions or electrons) formed from the combustion of the chemical substance in the flame chamber 10a are repelled by the elecrically biassed igniter 13, and are collected by the chamber walls; the current is fed to the current amplifier via cable 15 to produce pulsed ion current which is amplified and processed by a processor 16 A shield and electrical feedthrough holder, schematically indicated at 17, holds all the electrical connections from the power supply 13a to the igniter 13, and from the processor 16 to the collector 15.

As one example, the flame chamber 10a may have an inner diameter of 3 mm, and a length of 5 mm; the fuel from source 11 may be hydrogen continuously fed at a flow rate of 1–3 cc/min; source 12 may be air or pure oxygen fed continuously at a rate of 2 cc/min; igniter 13 may be a continuously-heated nickel-chromium wire; the rate of the flame pulses may be 3 Hz, and the pulse duration may be 0.5 msec with air, or 0.3 msec with pure oxygen.

It will be appreciated that the flow rate of the combustible gasses from sources 11 and 12, in order to produce a pulsed flame, is much lower than in the conventional flame detector wherein the rate sustains a continuous flame. Thus, in the pulsed flame technique illustrated in FIG. 1, as soon as the mixture of combustible gasses, including the chemical substance to be detected, reaches the natural ignitable concentration, the mixture is ignited by the continuously-heated igniter 13 to produce a flame which is propagated towards the opposite end of the flame chamber at a velocity sufficiently high, as compared to the rate of feed of the combustible gasses into the flame chamber, sufficiently to completely burn the combustible gasses, thereby self-terminating the flame. The concentration of combustible gasses then again increases to the point where it is again ignited by the igniter 13. Accordingly, the flame pulse repetition rate is directly dependent on the total gas flow rate, and is inversely dependent on the enclosed volume.

Using a continuously heated wire for the igniter 13 provides a very simple ignition, and also allows the highest repetition rate and total combustion. However, in some applications, the igniter may be intermittently energized, e.g., by including in the power supply 13a a capacitor which is periodically discharged across the igniter 13, or by using a pulsed laser, a pulsed lamp, or a pulsed spark plug, for igniter 13. Typical igniter wire is made of Ni/Cr alloy, platinum, or Pt/Rh alloy. A small auxiliary continuous butane flame can also serve as a flame igniter.

The use of the pulsed flame ionization detector shown in FIG. 1 has been studied with respect to a mixture of several organic molecules, and the obtained chromatogram has been compared with that obtained with the conventional continuous flame ionization detector. The observed relative line heights are practically identical indicating that the chemicalionization processes are basically similar under pulsed flame operation as under continuous flame operation. However, it has also been found that the addition of heteroatom, such as iodine, bromine or chlorine, results in a delayed ionization signal and thus adds a new dimension of information.

A peak-current increase by up to a factor of 300 has been measured. This pulsed-current increase, and the elimination of long term drifts and DC offsets, practically eliminate the effects of electronic amplifier noise in the detection. However, unless ultra-clean gasses are used, small organic impurities give rise to similarly amplified pulses of stray ions. The resulting picture is that the pulsed flame ionization detector is only as sensitive as the conventional continuous flame detector.

However, in cases where ultra-pure gasses are used, or where hydrogen consumption must be minimized, the pulsed flame detector possesses important advantages as discussed above. These advantages can be translated into a very simple mobile detector, powered by hydrogen from water-electrolysis (or another source). A simple signal processing would include current to voltage conversion, high pass electronic filtering, AC-DC voltage conversion, and low pass (time constant) electronic final filtering.

Figure 2:
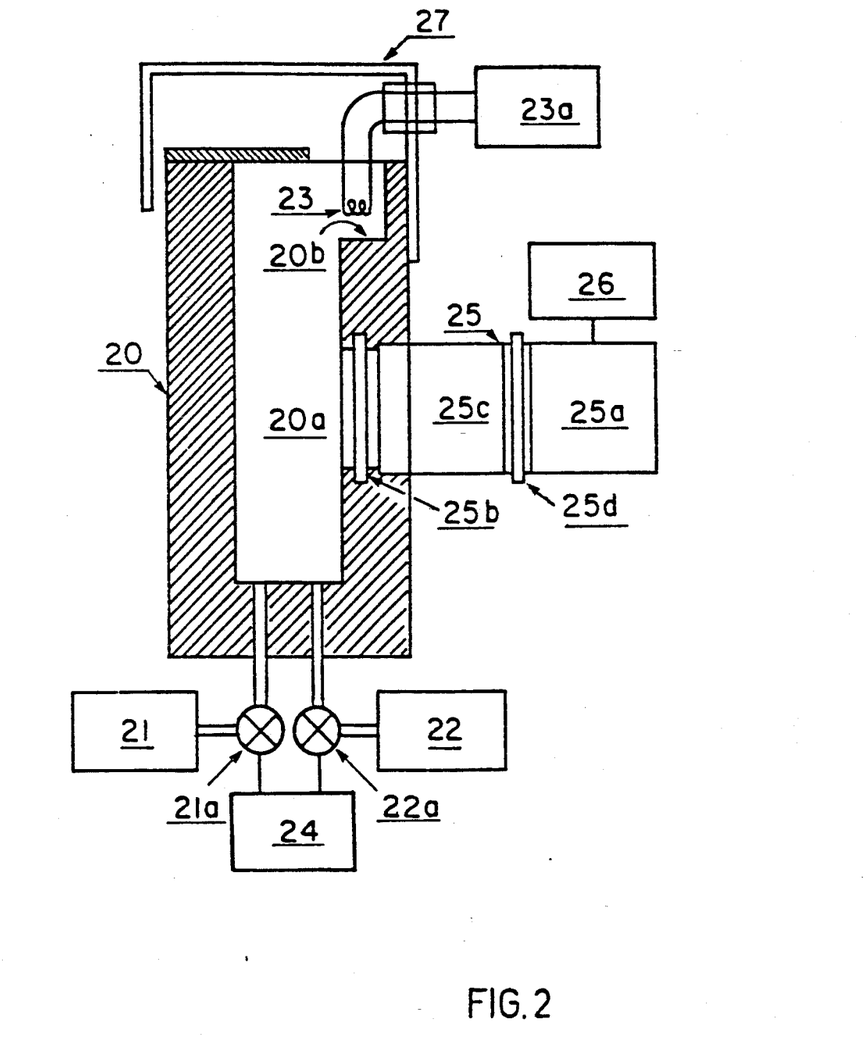
FIG. 2 is a schematic diagram of a pulsed flame photometer detector (PFPD) constructed in accordance with the invention.

FIG. 2 illustrates the invention embodied in a pulsed flame photometer detector (PFPD), generally designated 20, including a flame chamber 20a supplied by a mixture of combustible gasses from sources 21 and 22 under the control of valves 21a, 22a, respectively. As described above with respect to FIG. 1, the chemical substance to be detected may be included in source 21 or source 22, or may be injected directly into the flame chamber 20a separately. As also described above with respect to FIG. 1, the flame chamber 20a further includes an igniter 23 energized by a power supply 23a. A control unit 24, can also control the feeding of the combustible gas mixture into the flame chamber at a rate to produce the pulsed flame.

In the case of the pulsed flame photometer detector illustrated in FIG. 2, the detected characteristic is not the charged carriers (positive or negative ions or electrons), but rather electromagnetic radiation, particularly temporal light (which may be UV, visible or IR) emitted from the pulsed flame.

Thus, in FIG. 2 the light emitted from the pulsed flame is detected by an optical detection system 25. This optical system includes a photomultiplier 25a optically communicating with the interior of the flame chamber 20a via a sapphire window 25b, a light guide or lens optics (e.g., quartz or glass) 25c, and a filter 25d. Photomultiplier 25a outputs a pulsed signal which is processed by a processor 26 and may be plotted versus time. The light received by photomultiplier 25a is shielded against ambient (external) light by a light shield 27, and against the light from igniter 23 by a shielding wall 20b formed in the flame chamber.

Figure 2A:
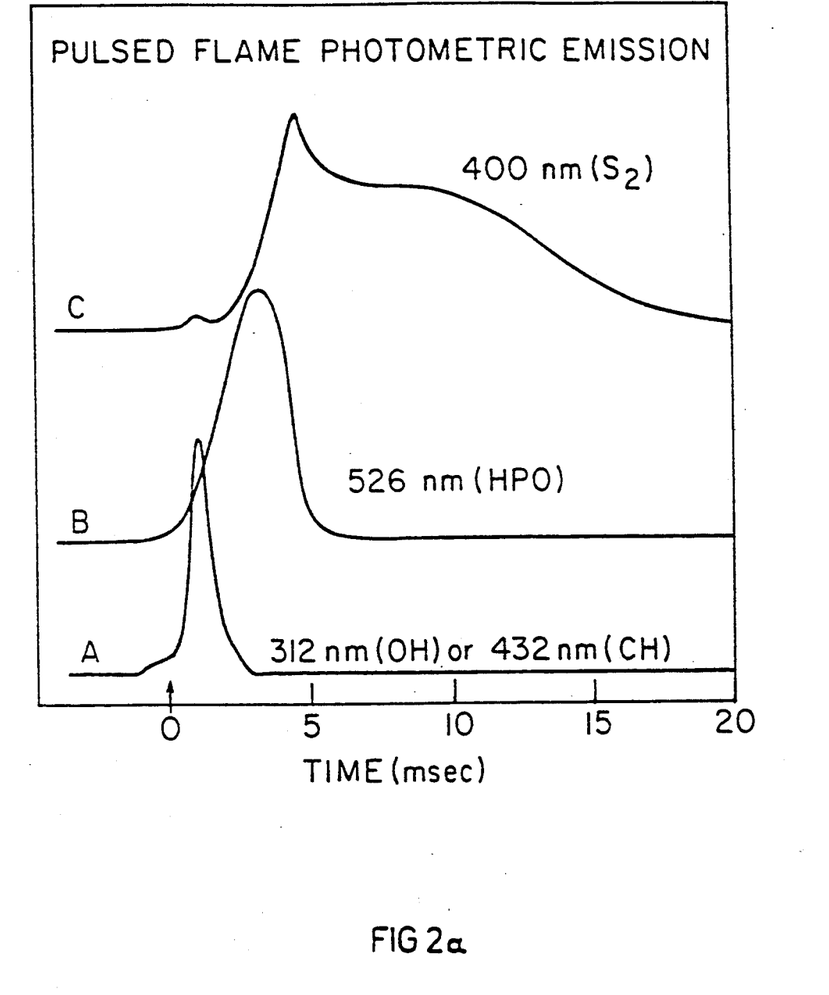
FIG. 2a is a graph illustrating a pulsed flame photmetric emission through a monochromator with respect to time.

FIG. 2a illustrates the characteristic temporal light emission behaviour in a hydrogen-rich pulse flame photometer detector constructed in accordance with FIG. 2.

Trace A shows the light emission as viewed through a monochromator. The emission plotted emerged from a pulsed flame of $H_2$/air at 312 nm (OH emission). Practically identical time dependence was obtained from cyclohexane seeded in the flame at 432 nm (CH emission). The ion pulses collected on the heated igniter served for triggering. As shown, the light emission is pulsed, and the pulses are short (—1 msec).

Trace B was obtained by viewing the phosphorus HPO emission at 526 nm from the combustion of 0.1% dimethylmethylphosphonate (DMP) in cyclohexane seeded in $H_2$/air flame. The main observation is that the pulsed light emission can be totally separated in time from any hydrocarbon background emission.

Trace C shows the emission of 0.1% of a sulfur compound dimethylsulfoxide (DMSO) seeded in $H_2$/air flame at 400 nm. The emission of $S_2$ has structure in time and is broader and further delayed than that of phosphorus compounds.

Figure 3:
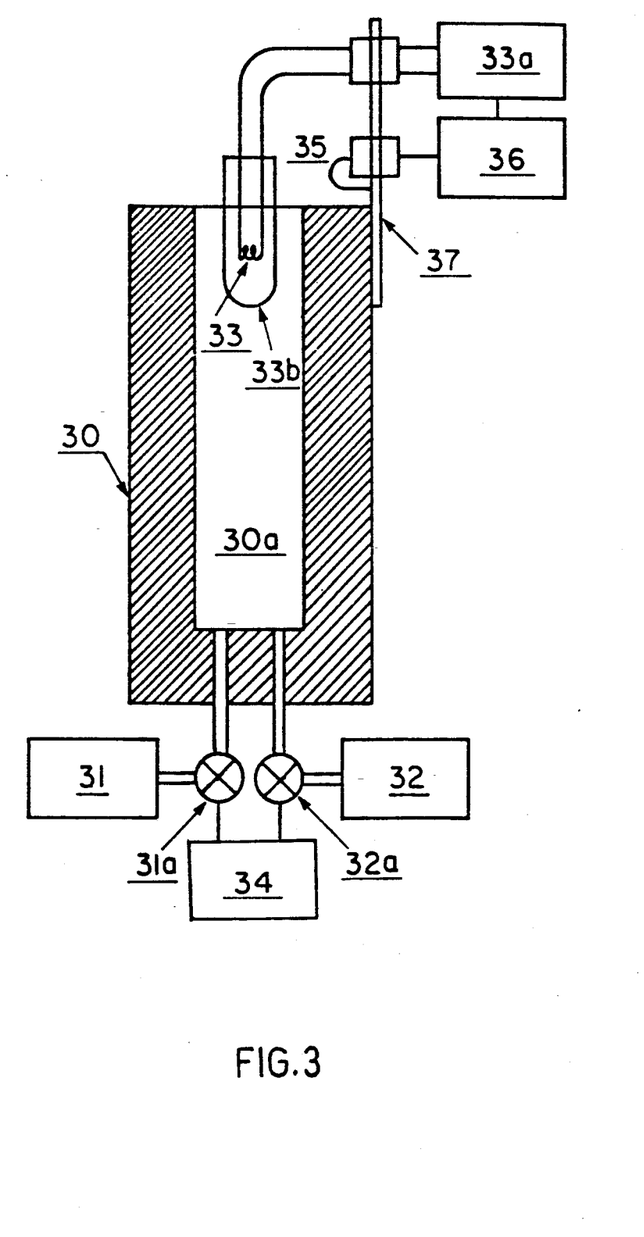
FIG. 3 is a schematic diagram of a pulsed flame thermionic ionization detector (PTID) constructed in accordance with the invention.

This unique feature of time dependence of the pulsed signal is a very important advantage of pulsed flames that distinguishes it from continuous flames and adds a new dimension of time information. In addition to its elemental dependence, the time dependence of the signal induced by the pulsed flame can be controlled by the combustible gas mixture, the detector structure and temperature, and the total gas pressure At lower pressures, the differences in the emissions as illustrated in FIG. 3 should be even more pronounced.

A pulsed flame photometer detector as illustrated in FIG. 2 is a highly selective and sensitive detector. In addition, as shown in FIG. 2a, time separation can be used with the aid of a gated amplifier or appropriate computer software to avoid chemical noise from most of the flame impurities. Thus further increase in sensitivity (lower moise), as well as a much better selectivity, is achieved. The selectivity increase can be translated into higher sensitivities due to the reduced chemical noise; also, one can replace the costly narrow band optical interference filter by a broad band coloured glass filter. Thus, the pulsed light signal is further improved by an order of magnitude. The higher corresponding increase in the early time hydrocarbon emission is irrelevant as it is filtered electronically by delayed time gating. The pulsed flame operation therefore may result in two orders of magnitude sensitivity and selectivity increase, as was measured in our laboratory.

Laboratory experiments have achieved a selectively of over $10^{+7}$ for both sulfur and phosphorus against carbon. This value is believed to be the highest reported. This time separation and increased peak light emission can broaden the scope of flame photometry as a selective detector of many other elements. For example, the pulsed flame photometer detector (FIG. 2) can serve as an organic-molecule detector with sensitivity comparable to that of the continuous flame ionization detector, or as a nitrogen selective detector, etc. The pulsed flame photometer detector of FIG. 2 has been operated in the nitrogen selective mode by detecting HNO* delayed emission at 680–780 nm. The selectivity against carbon was over $10^{+5}$, and the detection limits were in the low picogram nitrogen/sec. In fact, the time separation allows the parallel detection of many elements or molecular types, and a simple pattern recognition algorithm can be used for elemental identification.

In the case of nonlinear light emission, such as the case of sulfur, the gain in pulsed operation is even larger than the pulse duty cycle The gain of two to three orders of magnitude in the temporal light emission may be translated into a simpler and cheaper design by the use of a silicon photodiode instead of the more expensive and delicate photomultiplier and its high-voltage power supply. The possible reduction in hydrogen consumption also contributes to a much smaller and lighter detector. The time separation shown in FIG. 2a allows the total separation in time of heteroatom emission, such as sulfur and phosphorus, from that of organic molecules. Thus, the FIG. 2 detector can be used for the detection of liquid chromotograph or superfluid chromatograph where the organic mobile phase creates a severe background problem. In fact, it can be used even for the detection of sulfur in unseparated mixtures, such as oil, etc. The overall result is that this pulsed flame detector is more sensitive, selective, lighter and cheaper than the continuous flame photometer detector.

In using the pulsed flame photometer detector illustrated in FIG. 2 for detecting infrared (IR) light, the optical system 25 would be an IR system. Such a detector may be used particularly for the detection of CO, $CO_2$, halogen-containing molecules, and others, and can increase the sensitivity of the conventional continuous flame infrared detector by more than two orders of magnitude.

FIG. 3 illustrates a pulsed flame thermionic ionization detector, generally designated 30, including a flame chamber 30a fed by the chemical substance to be detected together with a mixture of combustible gasses from sources 31, 32 under the control of valves 31a, 32a, as described above with respect to FIG. 1. Such a detector also includes an igniter 33 energized by power supply 33a, a valve control unit 34, a charge collector 35 which is connected to the pulsed flame chamber producing an output supplied to a processor 36, and an electrical shield and feedthrough holder 37 all as described above with respect to FIG. 1.

The main difference in the detector illustrated in FIG. 3 from that of FIG. 1 is that the FIG. 3 detector includes an electrically heated surface 33b having a relatively low work-function as the active ionization element. This element can serve as both the ionization element, and also as the pulsed flame igniter 33. The pulsed flame igniter 33 can also be separated from the ionization surface to allow a lower temperature active surface as is encountered in the conventional TID. Negative ion and electron signals outputted by the charge collector 35 are separated in time and thus permit operation as both a pulsed flame ionization detector and as a pulsed flame thermionic ionization detector.

In the detector illustrated in FIG. 3, the pulsed flame may produce radicals such as CN and $PO_2$, even when conventional organic fuel is used. The ions that are formed by the combustion will be collected within about a millisecond, and the neutral species will be ionized later on the ceramic (or glass) surface. In this case the pulsed mode is used both to increase the sensitivity as well as the selectivity. In addition, the consumption of hydrogen gas can be reduced or totally eliminated by the use of organic fuel.

One of the best ways to detect sulfur-containing molecules is by their combustion to $SO_2$ followed by monitoring their lamp-induced fluorescence. The use of a pulsed flame and a pulsed lamp can considerably improve the detection sensitivity, or it can allow the use of a silicon photodiode as a detector instead of the more expensive and delicate photomultiplier. Detection sensitivity is enhanced for the following reasons: 1) Since both the $SO_2$ formation and exciting light are pulsed, the peak signal is considerably enhanced. 2) The photomultiplier dark current can be reduced by the use of a gated amplifier, while lamp generated stray light can be separated in time by the use of a 1–5 $\mu$sec pulsed lamp. The fluorescence decay time of $SO_2$ (and $NO_2$) is much longer ($-100$ $\mu$sec).

Additionally, trace metal atoms can be detected by using a standard continuous hollow cathode lamp as used in atomic absorption instruments to produce atomic line emission. The separation of the lamp induced fluorescence from the flame emission in time can significantly increase the detection sensitivity and reduce interferences as well as permitting electronic background subtraction.

Figure 4:
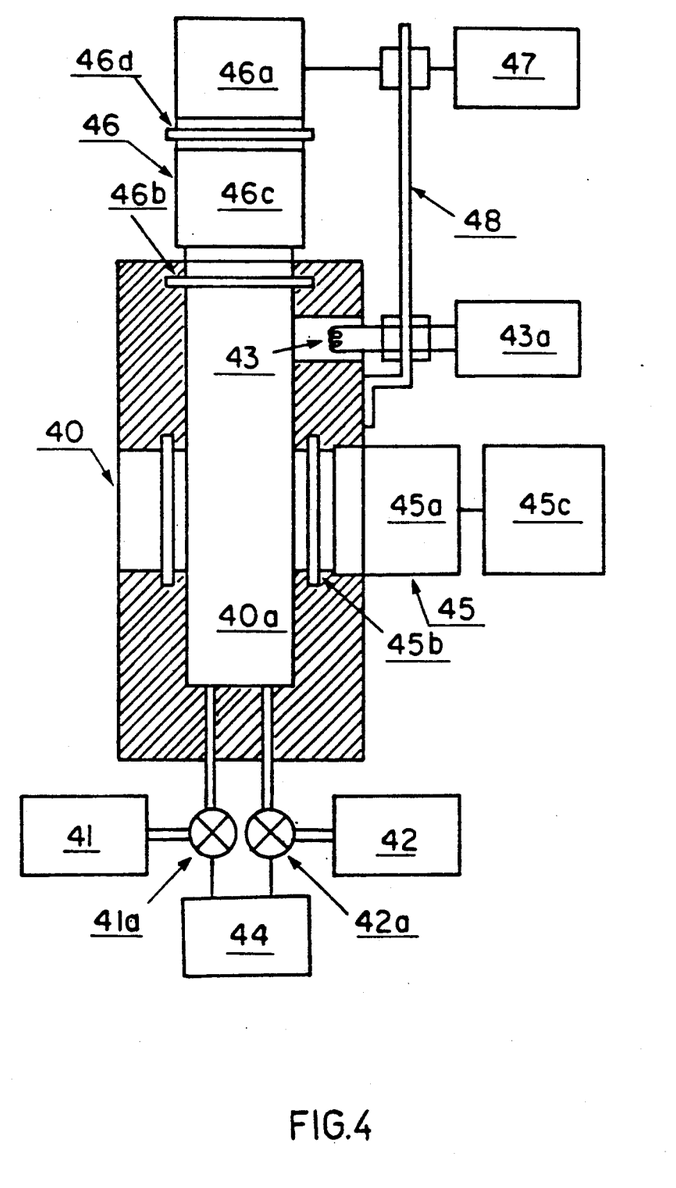
FIG. 4 is a schematic diagram of a pulsed flame induced flourescence (PFIF) detector constructed in accordance with the invention.

A pulsed flame induced-fluorescence detector is schematically illustrated in FIG. 4. Such a detector is similar to the photometer detector illustrated in FIG. 2, with the addition of a pulsed or continuous lamp (laser) excitation system.

Thus, the detector illustrated in FIG. 4, therein generally designated 40, includes a flame chamber 40a fed with the chemical substance to be detected and the combustible gasses from sources 41, 42 via their respective valves 41a, 42a, controlled by the control unit 44 and ignited by an igniter 43, energized by power supply 43a, as described above with respect to FIG. 2. The detector in FIG. 4 further includes a pulsed or continuous light-producing system, generally designated 45, including a pulsed (e.g., a laser) or continuous light source 45a, a window 45b to the flame chamber 40a, and a power supply 45c.

The lamp-induced fluorescence light emission affected by the pulsed flame within chamber 40a is detected by a detection system, generally designated 46, similar to the light detection system 25 in FIG. 2, and including a photomultiplier 46a, a sapphire window 46b, a light guide 46c and a filter 46d. The output from the photomultiplier is fed to a processor 47. A shield 48 serves both as a light and electrical shield and feedthrough holder.

After the pulsed flame ignition (as described above), the light source 45a is energized by control unit 45c and illuminates the flame products through the window 45b. The fluorescence is detected by the optical detection system 46, and its output is processed by the processor 47, as described above with respect to FIG. 2.

The pulsed flame emitted light (OH* or organic impurities-CH*) can serve for triggering, which may be delayed to avoid chemiluminescence. This time delay can also simplify the construction, since the requirement of a separated combustion chamber is avoided.

Figure 5:
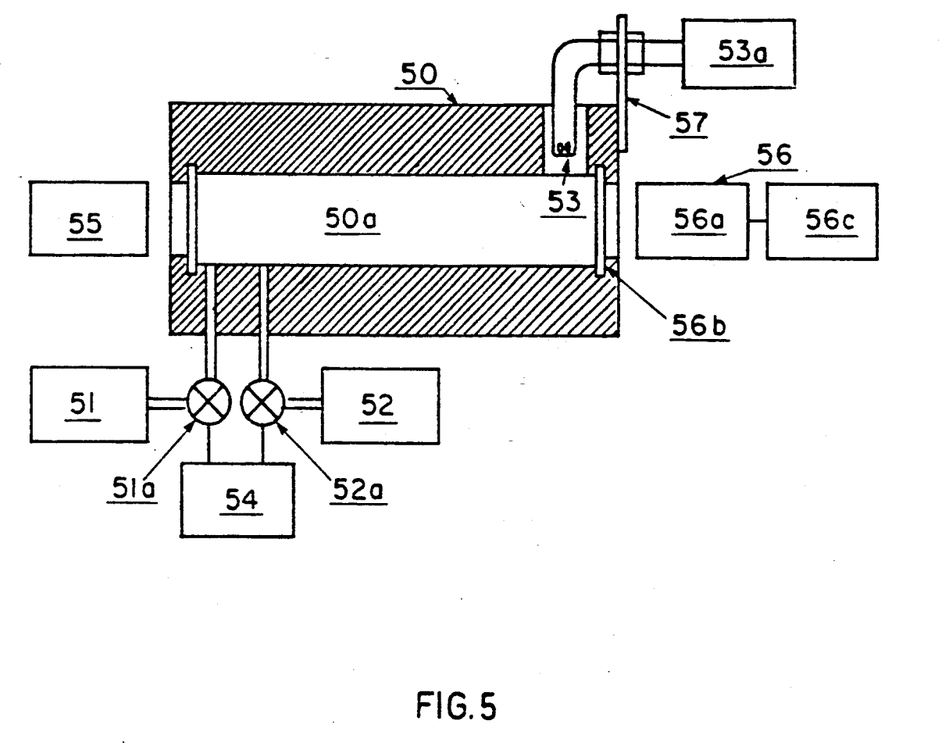
FIG. 5 is a schematic diagram of a pulsed flame atomic absorption detector (PFAAD) constructed in accordance with the invention.

FIG. 5 illustrates the above-described pulsed flame technique implemented in a flame atomic absorption detector 50. Such detector includes a flame chamber 50a supplied with the chemical substance to be detected (usually in an aerosol with the fuel or air), and a mixture of combustible gasses from sources 51, 52 via valves 51a, 52a respectively, under the control of the valve control unit 54 and ignited by an igniter 53 energized by power supply 53a, as described earlier. In this case, a light source 55 illuminates through the flame chamber 50a, and the opposite end is provided with a detector system 56, including a photomultipler 56a and window 56b, for detecting the attenuation of the light from source 55 produced by the action of the pulsed flame within chamber 50a. The output of detector 56a is supplied to a processor 56c. An electrical shield and feedthrough holder 57 contains the connection from the power supply 53a to the igniter 53.

As one example, the fuel source 51 could be acetylene having the chemical susbstance to be detected mixed therein in the form of an aerosol, and source 52 could be air, oxygen or $N_2O$. Lamp 55 should be an atomic line emitting lamp, such as a hollow cathode lamp. This light passes through the pulsed flame products and its absorption is detected by detector 56a and processed by processor 56c.

The light attenuation is a measure of the number of atoms in the flame. The identity of the atoms is determined by the atomic line selected. The use of a pulsed flame can aid in the following: a) increase the atom concentration and optical density for a short time. b) eliminate DC and long-term drifts. c) allow for the time separation in order to avoid interference from flame fluorescence and excited or ionized species. Obviously this concept can be extended to molecular detection and infrared absorption monitoring of the flame products.

The above-described pulsed flame technique can also allow the introduction of new and powerful detection schemes which do not exist with continuous flame techniques, but which are made possible and attractive with pulsed flame techniques. Two examples are described below.

One example is related to the ion mobility spectrometer (IMS), which recently has found an increasing number of applications. It is based on sample ionization usually with the aid of radioactive nickel followed by charge exchange and pulsed ion extraction. The time of arrival of ions to the detector is measured and is inversely dependent on the ion mobility, which generally decreases with increase in the ion mass.

Figure 6:
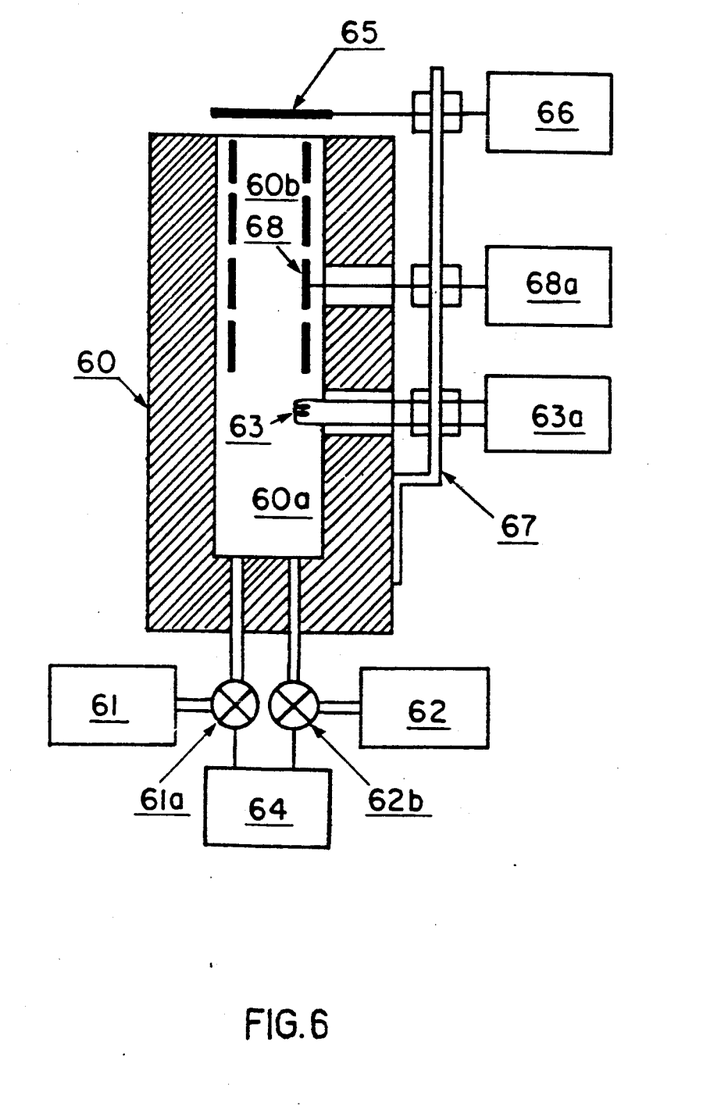
FIG. 6 is a schematic diagram of a pulsed flame ion mobility spectrometer (PFIMS) constructed in accordance with the invention.

FIG. 6 illustrates the pulsed flame technique implemented in an ion mobility spectrometer of the foregoing type. Such detector also includes a flame chamber 60a supplied with the chemical substance to be detected mixed in a combustible gas mixture fed by sources 61, 62 via their respective valves 61a, 62a, under the control of valve control unit 64 and an igniter 63 energized by power supply 63a, as described above with respect to FIG. 1. The ions are collected in an ion collector 65 at the end of the chamber outputting an electrical signal to a processor 66. A feedthrough holder 67 also electrically shields the electrical connection of power supply 63a with its igniter 63 and the electrical connection of the processor 66 with the ion collector 65.

In the detector illustrated in FIG. 6, however, a part of the flame chamber 60a is provided with an ion drift region 60b subjected to a voltage gradient by electrodes 68 energized by a voltage power supply 68a. As one example, a pulsed flame of butane (or other organic fuel) from source 61, and oxygen or air from source 62, will produce, after ignition by igniter 63, a high density of electrons in the small flame chamber 60a. These electrons will be attached to flame-produced electronegative radicals, such as $PO_2$, CN, Cl, $PbO_2$, $SiO_2$, etc. These ions will move in the ion drift region 60b produced by the electric field generated by electrodes 68 and power supply 68a to the ion collector 65, and their time of arrival will be measured by processor 66.

The pulsed flame ion mobility spectrometer illustrated in FIG. 6 may thus serve as an entirely selective and sensitive functional-group (or atom) detector. Actually, any pulsed flame ionization detector can be operated as a crude pulsed flame ion mobility spectrometer by the time separation of negative ions from the much faster electrons, or by the employment of a delayed negative ion collection voltage pulse to the ion drift region 60b. The pulsed flame ion mobility spectrometer illustrated in FIG. 6 is thus an ion mobility spectrometer with a pulsed flame serving as a high density electron source and a high electron affinity species generator. It can also be used as a high density pulsed electron source in ion mobility spectrometers to replace the radioactive nickel element, and to produce either negative or positive ions in the usual way when the sample is fed outside the organic fuelled pulsed flame.

Figure 7:
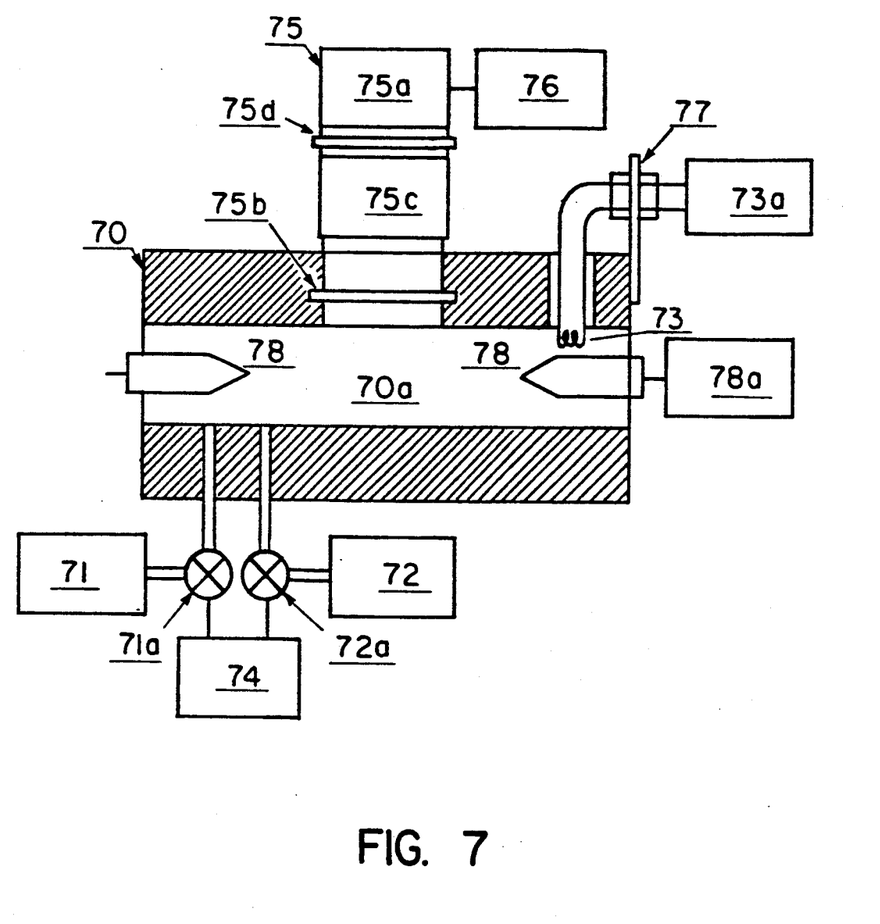
FIG. 7 is a schematic diagram of a pulsed flame-plasma emission detector (PFPED) constructed in accordance with the invention.

Another new application of the pulsed flame technique is in a plasma-induced atomic-emission detector as illustrated in FIG. 7. Such detectors have recently become of increasing importance in spite of their relatively high cost because of their possible use as universal atom-selective detectors.

The detector illustrated in FIG. 7, therein generally designated 70, is similar to that illustrated in FIG. 2. It includes a flame chamber 70a supplied with the chemical substance to be detected in a mixture of combustible gasses fed from sources 71, 72 via valve 71a, 72a under the control of valve control unit 74 and ignited by an igniter 73, as described above with respect to FIG. 2. In addition, the detector includes an optical system 75 comprising a photomultiplier 75a, viewing the interior of the flame chamber 70a via a sapphire window 75b, a light guide 75c, and a filter 75d, and providing an output to a processor 76. Alternatively, the filter is replaced by a monochromator; and the light detecting element may be a diode array for the parallel multi-element detection. The feedthrough holder 77 also optically shields the light detector system 75 from the ambient light.

The detector illustrated in FIG. 7 further includes a pair of discharge electrodes 78 on opposite sides of the flame chamber 70a, and energized by a power supply 78a. Power supply 78a includes a capacitor which discharges across the two electrodes 78, to produce a plasma within chamber 70a, after a predetermined time following the ignition of the pulsed flame within chamber 70a.

When the flame is pulsed, a large current of positive ions and electrons is formed especially if organic fuel is also introduced. This current can trigger the discharge of the capacitor in the power supply 78a to promote the plasma emission. Thus, the atomic emission is pulsed with a much higher peak light emission (because of the higher atom concentration and higher plasma temperature), which makes it easier to detect. In addition, the flame can aid in the dissociation and combustion of molecules, and thus both molecular effects and the required plasma-electrical power consumption can be reduced. Time separation can also aid in cases of atomic phosphoresence.

While the invention has been described with respect to a number of embodiments, it will be appreciated that these are set forth merely for purposes of example. It will also be appreciated that the detector may detect more than one characteristic, e.g., the light emitted, and the ions generated, in a dual pulse-flame ionization and photometer detector. Many other variations, modifications and applications of the invention will be apparent.

What is claimed is:

1. A flame method of analyzing a sample by introducing the sample into a combustible gas mixture, igniting the combustible gas mixture to produce a flame, and detecting a characteristic of the resulting flame to determine the identity and/or concentration of one or more chemical substances in the sample, characterized in that said flame is a pulsed flame.

2. The method according to claim 1, wherein said sample and combustible gas mixture are continuously introduced into a flame chamber having a continuously energized igniter and having a volume which allows flame propagation in the chamber at a rate which, compared to the rate of introduction of the combustible gas mixture, causes the flame to self-terminate and then to reignite, to thereby produce said pulsed flame.

3. The method according to claim 1, wherein the combustible gas mixture is fed under the control of pulsed-operated valve means, to thereby produce said pulsed flame.

4. The method according to claim 1, wherein said combutible gas mixture is ignited by pulsed-energized igniter means, to thereby produce said pulsed flame.

5. The method according to claim 1, wherein said detected characteristic is charge carriers formed by said pulsed flame.

6. The method according to claim 1, wherein said detected characteristic is electromagnetic radiation emitted from said pulsed flame.

7. The method according to claim 1, wherein said detected characteristic is thermionic ions affected by said pulsed flame.

8. The method according to claim 1, wherein said detected characteristic is light induced fluorescence induced by said pulsed flame.

9. The method according to claim 1, wherein said detected characteristic is atomic absorption resulting from said pulsed flame.

10. The method according to claim 1, wherein said detected characteristic is ion formation in an ion mobility spectrometer by said pulsed flame.

11. The method according to claim 1, wherein said detected characteristic is the effect on plasma induced light emission by said pulsed flame.

12. The method according to claim 1, wherein said detected characteristic is processed in the pulse mode coordinated with the pulses of said pulsed flame.

13. The method according to claim 1, wherein the flame is selectively controlled to operate either according to a pulsed flame mode or according to a continuous flame mode.

14. The method according to claim 1, wherein trapping and desorption of sample molecules is performed between the flame pulses.

15. The method according to claim 1, wherein the durations of said flame pulses are from 40 microseconds to 40 milliseconds, and their frequency is up to 200 Hz.

16. The method according to claim 1, wherein said pulsed flame is pulsed periodically.

17. The method according to claim 1, wherein said pulsed flame is pulsed aperiodically.

18. A flame based detector for use in analyzing a sample in order to determine the identity and/or concentration of one or more chemical substances therein, comprising: feeding means for feeding the sample into a combustible gas mixture, an igniter for igniting the combustible gas mixture to produce a flame, and a detector means for detecting a characteristic of the resulting flame to determine the identity and/or concentration of one or more chemical substances in the sample; characterized in that said apparatus includes control means for pulsing said flame.

19. The apparatus according to claim 18, further including a flame chamber into which the combustible gas mixture, including the sample, is fed; said control means including means for continuously energizing said igniter, and means for controlling said feeding means to feed the combustible gas mixture into said flame chamber at a lower rate than the flame velocity such as to cause the flame to self-terminate, and then to reignite, to thereby produce said pulsed flame.

20. The apparatus according to claim 18, wherein said control means includes pulse-operated valves in said feeding means for feeding the combustible gas mixture in pulses, to thereby produce said pulsed flame.

21. The apparatus according to claim 18, wherein said control means includes means for energizing said igniter in pulses, to thereby produce said pulsed flame.

22. The apparatus according to claim 18, wherein said detector is one which detects charge carriers formed by said pulsed flame.

23. The apparatus according to claim 18, wherein said detector is one which detects electromagnetic radiation emitted from said pulsed flame.

24. The apparatus according to claim 18, wherein said detector is one which detects species generated by said pulsed flame.

25. The apparatus according to claim 18, wherein said detector is one which detects thermionic ions affected by said pulsed flame.

26. The apparatus according to claim 18, wherein said detector is one which detects light induced fluoresence induced by said pulsed flame.

27. The apparatus according to claim 19, wherein said detector is one which detects atomic absorption resulting from said pulsed flame.

28. The apparatus according to claim 18, wherein said detector is one which detects ion formation by said pulsed flame in an ion mobility spectrometer.

29. The apparatus according to claim 18, wherein said detector is one which detects plasma induced light emission as affected by said pulsed flame.

30. The apparatus according to claim 18, wherein the output of said detector is processed in the pulsed mode coordinated with the pulses of said pulsed flame.

31. The apparatus according to claim 18, wherein said control means selectively controls the apparatus to operate either according to a pulsed flame mode or according to a continuous flame mode.

32. The apparatus according to claim 18, wherein said control means produces flame pulses having durations of from 40 microseconds to 40 milliseconds, with a frequency of up to 200 Hz.

33. The apparatus according to claim 18, wherein said control means pulses said flame periodically.

34. The apparatus according to claim 18, wherein said control means pulses said flame aperiodically.

* * * * *